United States Patent [19]

Venier et al.

[11] Patent Number: 5,144,095
[45] Date of Patent: * Sep. 1, 1992

[54] SUBSTITUTED CYCLOPENTADIENES, METHODS OF MANUFACTURE AND USES

[75] Inventors: Clifford G. Venier; Edward W. Casserly, both of The Woodlands, Tex.

[73] Assignee: Pennzoil Products Company, Houston, Tex.

[*] Notice: The portion of the term of this patent subsequent to Jul. 18, 2006 has been disclaimed.

[21] Appl. No.: 660,469

[22] Filed: Feb. 25, 1991

Related U.S. Application Data

[60] Continuation-in-part of Ser. No. 323,749, Mar. 15, 1989, Pat. No. 5,012,022, which is a continuation of Ser. No. 170,654, Mar. 15, 1988, abandoned, which is a division of Ser. No. 112,378, Oct. 22, 1987, Pat. No. 4,849,566, and a continuation-in-part of Ser. No. 323,164, Mar. 15, 1989, Pat. No. 4,929,782, which is a continuation of Ser. No. 170,653, Mar. 15, 1988, abandoned, which is a division of Ser. No. 112,378, Oct. 22, 1987, Pat. No. 4,849,566, and a continuation-in-part of Ser. No. 323,906, Mar. 15, 1989, Pat. No. 5,012,021, which is a continuation-in-part of Ser. No. 170,652, Mar. 18, 1988, abandoned, which is a division of Ser. No. 112,378, Oct. 22, 1987, Pat. No. 4,839,566, which is a continuation-in-part of Ser. No. 909,305, Sep. 19, 1986, Pat. No. 4,721,823.

[51] Int. Cl.$^5$ .............................................. C07C 2/86
[52] U.S. Cl. ................................ 585/20; 585/375; 585/467
[58] Field of Search .................. 585/20, 23, 359, 375

[56] References Cited

U.S. PATENT DOCUMENTS

| | | |
|---|---|---|
| 2,088,598 | 8/1937 | Ipatieff et al. . |
| 2,276,203 | 3/1942 | Kharasch . |
| 2,448,641 | 9/1948 | Whitman . |
| 2,953,607 | 9/1960 | Hafner . |
| 3,000,981 | 9/1961 | Favis . |
| 3,004,384 | 10/1961 | Saunders . |
| 3,131,227 | 4/1964 | de Vries . |
| 3,214,483 | 10/1965 | Cripps . |
| 3,251,897 | 5/1966 | Wise . |
| 3,255,267 | 6/1966 | Fritz et al. . |
| 3,356,704 | 12/1967 | Marcus . |
| 3,358,008 | 12/1967 | Marcus et al. . |
| 3,388,180 | 6/1968 | Marcus et al. . |
| 3,391,209 | 7/1968 | Marcus . |
| 3,403,105 | 9/1968 | Sandri . |
| 3,414,626 | 12/1968 | Marcus . |
| 3,419,622 | 12/1968 | Marcus et al. . |
| 3,560,583 | 2/1971 | Stewart, Jr. . |
| 3,636,176 | 1/1972 | Hall . |
| 3,751,500 | 8/1973 | Hall . |
| 3,755,492 | 8/1973 | Anderson . |
| 3,931,334 | 1/1976 | Gemmill, Jr. . |
| 4,063,010 | 12/1977 | Marie et al. . |
| 4,147,640 | 4/1979 | Jayne et al. . |
| 4,246,373 | 1/1981 | Kennedy et al. . |
| 4,412,088 | 10/1983 | Gruber et al. . |
| 4,547,603 | 10/1985 | Rajan . |
| 4,567,308 | 1/1986 | Yoshida et al. . |
| 4,604,492 | 8/1986 | Shimizu et al. . |
| 4,721,823 | 1/1988 | Venier et al. . |
| 4,814,532 | 3/1989 | Yoshida et al. . |
| 4,849,566 | 7/1989 | Venier et al. . |
| 4,929,782 | 5/1990 | Venier et al. . |
| 5,012,022 | 4/1991 | Venier et al. ............... 585/20 |
| 5,012,023 | 4/1991 | Venier et al. ............... 585/20 |

FOREIGN PATENT DOCUMENTS

WO88/01994 3/1988 PCT Int'l Appl. .
55535 9/1968 Poland .
55571 9/1968 Poland .

OTHER PUBLICATIONS

Chemical Journal of Chinese Universities, 1983, vol. 41 (10), pp. 971–973.
Journal of American Chemical Society in 1990, vol. 112, pp. 2807–2809.
Henri et al., "Bulletin de la Societe Chimique France," 1976, No. 11–12, pp. 1861–1864.
Weber et al., "Phase Transfer Catalysis and Organic Synthesis," pp. 6, 140 and 201, published by Springer-Verlag, Berlin, Heidelberg, New York, 1977.
Sitzmann, Zeitschrift fur Naturforschung, B44 1989, pp. 1, 2, 4–7.
"Chemical and Engineering News" Sep. 24, 1990, p.2.
Tolman, C. A., Chem. Rev. 1977, 77, p. 313.
Heeg, M. J.; Janiak, C.; Zuckerman, J. J. J. Am. Chem. Soc. 1984, 106, 4259 and references therein.
Chambers, J. W.; Baskar, A. J.; Bott, S.G.; Atwood, J. L.; Rausch, M. D. Organometallics 1986, 5, 1635.
Lorberth, J.; Shin, S.-H.; Wocadlo, S.; Massa, W. Angew Chem., Int. Ed. Engl. 1989, 28, 735 and references therein.
Dormond, A.; El Bouadili, A.; Moise, C. Tetrahedron Lett. 1983, 24, 3087.
Okuda, J.; Herdtweck, E. Chem. Ber. 1988, 121, 1899.
Okuda, J. Chem. Ber. 1989, 122, 1075.
Abu-Orabi, S. T.; Jutzi, P. J., Organomet, Chem. 1987, 329, 169.
Tumanov, A. A.; Zakharov, L. N.; Sennikov, P. G.; Egorochkin, A. N.; Razuvaev, G. A.; Smirnov, A. S.; Dodonov, V. A. J. Organomet. Chem. 1984, 263, 213.
Starks, C. M.; Liotta, C., Phase Transfer Catalysis; Academic Press; New York, 1978; p. 330.
Montanari, F.; Landini, D.; Rolla, F. Top. Curr. Chem. 1982, 101, 147–200, 184.

(List continued on next page.)

*Primary Examiner*—Asok Pal
*Attorney, Agent, or Firm*—Lowe, Price, LeBlanc & Becker

[57] ABSTRACT

Tertiary alkyl substituted cyclopentadienes are prepared by reaction of cyclopentadiene with a stoichiometric excess of a tertiary alkyl halide under phase transfer conditions. The tertiary-alkyl substituted cyclopentadienes are useful as synthetic lubricants.

11 Claims, No Drawings

OTHER PUBLICATIONS

Dehmlow, E. V.; Dehmlow, S. S., Phase Transfer Catalysis, 2nd ed.; Verlag Chemie; Deerfield Beach, Fl., 1983; p. 177.

Riemschneider, R.; Nehring, R. Monatsh. Chem. 1959, 90, 568–570.

Leigh, T. J. Chem. Soc. 1964, 3294–3302.

Riemschneider, R. Z. Naturforsch. B. 1963, 18, 641–645.

Schonholzer, S.; Slongo, M.; Rentsch, C.; Neuenschwander, M. Makromol. Chem. 1980, 181, 37–45.

Maier, G.; Pfriem, S.; Schafer, U.; Malsch, K.-D.; Matusch, R. Chem. Ber. 1981, 114, 3965–3987.

Rong et al., Journal of Chinese Universities, vol. 4, pp. 576–580 (1985).

Hirsch, Pyrolysis of olefins and base-catalyzed alkylation of cyclopentadienes, U. of Maryland Thesis, 1963.

Denis, Journal of Synthetic Lubrication 1, pp. 201–219 (1985).

Rong et al., Acta Chemica Sinica, vol. 41, No. 10, Oct., 1983, pp. 971–973.

SUBSTITUTED CYCLOPENTADIENES, METHODS OF MANUFACTURE AND USES

CROSS REFERENCE TO RELATED APPLICATIONS

This is a continuation-in-part of application Ser. No. 323,749 filed Mar. 15, 1989, now U.S. Pat. No. 5,012,022, which is a continuation of Ser. No. 170,654, filed Mar. 15, 1988, now abandoned, which i a division of Ser. No. 112,378, filed Oct. 22, 1987, now U.S. Pat. No. 4,849,566; and is a continuation-in-part of Ser. No. 323,164, filed Mar. 15, 1989, now U.S. Pat. No. 4,929,782, which is a continuation of Ser. No. 170,653, filed Mar. 15, 1988, now abandoned, which is a division of said Ser. No. 112,378; and is a continuation-in-part of Ser. No. 323,906, filed Mar. 15, 1989, now U.S. Pat. No. 5,012,023, which is a continuation-in-part of Ser. No. 170,652, filed Mar. 18, 1988, now abandoned, which is a division of said Ser. No. 112,378, said Ser. No. 112,378 being a continuation-in-part of Ser. No. 909,305, filed Sep. 19, 1986, now U.S. Pat. No. 4,721,823.

FIELD OF THE INVENTION

This invention relates to novel alkylated cyclopentadienes, their use as lubricating compositions, and methods of manufacture. More particularly, this invention relates to novel alkylated cyclopentadienes which are substituted by tertiary alkyl groups and their novel methods of formation by alkylation.

BACKGROUND

Cyclopentadiene and alkylated derivatives thereof are known in the art. Further, methods are known for preparation of alkylated cyclopentadienes. There is substantial interest in cyclopentadienes since this material is characterized by the unique property of being the most acidic aliphatic hydrocarbon known, having a pKa of 18 and also because its reactions as a Diels-Alder diene are extremely facile.

Because of the aromaticity of the cyclopentadiene anion, cyclopentadiene is easily the most acidic of the simple hydrocarbons and in fact is comparable in acidity to alcohols. This means that substantial amounts of the anion can be generated with alkyl oxides and even concentrated solutions of hydroxide. Since it is uniquely stable, it can participate in the caranion reactions of alkylation, acylation, carboxylation and the like.

U.S. Pat. No. 3,255,267 to Fritz et al. discloses the alkylation of cyclopentadiene and monoalkylcyclopentadiene with a single primary or secondary alcohol in the presence of a highly alkaline catalyst, including the disclosure of trialkylated and tetralkylated products. The cyclopentadienes described by Fritz et al contain primary hydrocarbon substituents of up to 11 carbon atoms and secondary hydrocarbons of structure $R_cR_dCH$, where $R_d$ is "a hydrocarbon radical free of aliphatic unsaturation, including alkyl and aryl radicals, said radicals having from 1 to 10 carbon atoms,". However, the process of Fritz cannot be used to produce t-alkyl substituted cyclopentadienes.

In a publication by Rong et al, Acta Chemica Sinica, Vol. 41, No. 10, October, 1983, there is disclosure of the use of polyethylene glycol as a phase transfer agent for halide alkylation of cyclopentadiene with alkyl halides. The products produced are monoalkyl substituted cyclopentadienes. In a related article by Rong et al, Journal of Chinese Universities, Vol. 4, pages 576–580 (1983), there is disclosure of the synthesis of alkyl substituted derivatives of cyclopentadiene by the phase transfer catalytic reaction of cyclopentadiene with alkyl halides in the presence of potassium hydroxide and polyoxyethylene surfactants as a catalyst. Only monoalkyl substituted cyclopentadienes are prepared.

U.S. Pat. No(s). 3,004,384, 3,356,704, 3,358,008, 3,388,180, 3,391,209, 3,414,626, and 3,419,622 disclose polysubstituted cyclopentadienes and cyclopentadienes but wherein the substituent is a short chain alkyl group or allyl group. U.S. Pat. No(s). 3,751,500 and 3,636,176 disclose indene compounds which can contain short chain alkyl substituents which are useful as perfume compositions.

U.S. Pat. No. 2,448,641 discloses the alkylaton of cyclic hydrocarbons by reaction of a cyclic hydrocarbon such as a cycloolefin with an olefin such as ethylene in the presence of heat, pressure and a metallic sodium catalyst.

U.S. Pat. No. 2,276,203 discloses the condensation of allyl halides with substituted allyl halides in the presence of alkali metal amides.

SUMMARY OF THE INVENTION

It is accordingly one object of the present invention to provide tertiary-alkyl substituted cyclopentadienes.

A further object of the invention is to provide novel tertiary-alkyl substituted cyclopentadienes. An even further object of the invention is to provide novel synthetic lubricant compositions comprising tertiary-alkyl substituted cyclopentadienes which may contain one or more lubricant additives.

A further object of the present invention is to provide a novel alkylation method for the preparation of tertiary-alkyl substituted cyclopentadienes.

Other objects and advantages of the present invention will become apparent as the description thereof proceeds.

In satisfaction of the foregoing objects and advantages, there are provided by the present invention novel tertiary-alkyl substituted cyclopentadienes of the following general formula:

wherein in the above formula, $R_1$ is selected from the group consisting of hydrogen and non-tertiary alkyl of one to four carbon atoms, and each $R_2$ is individually and independently selected from the group consisting of tertiary-alkyl groups of four to twelve carbon atoms and a is 2 or 3 with the proviso that when $R_1$ is H, a is 3. In the preferred embodiment, the tertiary carbon is attached to the ring.

Also provided by the present invention are novel synthetic lubricating compositions comprising the tertiary-alkyl substituted cyclopentadienes of this invention, or in combination with a lubricant additive.

Also provided by the present invention is a method for the preparation of the tertiary-alkyl cyclopentadienes of this invention which comprises the reaction of cyclopentadiene or an alkyl-substituted cyclopentadiene with a stoichiometric excess of a tertiary alkyl halide in the presence of a phase transfer catalyst such as a quaternary ammonium halide and a base such as NaOH,

DETAILED DESCRIPTION OF THE INVENTION

The present invention is broadly concerned with novel alkylated cyclopentadienes, use of those alkylated cyclopentadienes in lubricating compositions, or in combination with a lubricant additive, and novel methods for preparation of the alkylated cyclopentadienes. The invention is specifically concerned with a class of tertiary-alkyl substituted cyclopentadienes which may be described by the following general formula:

wherein in the above formula, each $R_1$ is selected from the group consisting of hydrogen and non-tertiary alkyl of one to four carbon atoms, each $R_2$ is individually and independently selected from the group consisting of tertiary-alkyl groups of four to twelve carbon atoms, and a is an integer of 2 or 3, with the proviso that when $R_1$ is hydrogen, a is 3.

A preferred group of cyclopentadienes of this invention are those of the following formula:

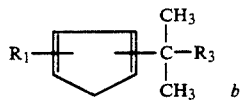

wherein $R_1$ is H or non-tertiary alkyl of one to four carbon atoms, $R_3$ is straight or branch chained alkyl of 2 to 9 carbon atoms, and b is 1 to 4, provided that when $R_1$ is H, b is at least 2.

The present invention also provides a synthetic lubricating composition comprising a tertiary alkyl substituted cyclopentadiene of the following formula:

wherein $R_1$ is hydrogen or an alkyl group of 1 to 4 carbon atoms, $R_2$ is a tertiary-alkyl group of 4 to 10 carbon atoms, and a is 1 to 5, providing that the number of carbons in $R_1$ plus a times the number of carbons in $R_2 \geq 12$.

The synthetic lubricating compositions of the present invention are used as lubricants by blending with one or more additives conventionally used with lubricating oil obtained from natural sources or other types of synthetic lubricating oil. Thus, there may be included within the synthetic lubricating oil of this invention from 0.01 up to about 40% by weight of conventional pour point depressants, viscosity index improvers, dispersants, load carrying agents, rust inhibitors, and antioxidants, as well as mixtures of such conventional additives. It will be understood that the synthetic lubricants of this invention will be mixed with the number of additives and amounts to provide good performance, particularly when used in internal combustion engines. Particular additives which may be used include polymethacrylates which are well known as pour point depressants and viscosity index improvers such as hydrogenated diolefin-lower alkyl acrylate or methacrylate copolymers. Other additives which may be blended with the lubricants of the invention include zinc dialkyl dithiophosphates, phenates, sulfonates, non-ionic dispersants, such as alkyl succinimides or Mannich bases of phenols, polyacrylate and methacrylate pour point depressants, and olefin copolymer or polyacrylate viscosity index improvers, or any other effective motor oil additives.

The synthetic lubricating oil of this invention may be blended in amounts ranging from about 5% to 95% with a lubricant obtained from natural sources such as a refined paraffin-type base oil, a refined napthenic-type base oil, asphaltic or mixed base crude and/or mixtures therof. The viscosity of such oils may vary over a wide range such as from 70 SUS at 100° F. to 300 SUS at 210° F. and the boiling point of these oils may vary over a wide range as from 300°-750° F.

The alkylated cyclpentadienes of the present invention are prepared by a unique phase transfer alkylation process using a tertiary-alkyl halide which has been found to provide unexpectedly high yields of high purity, i.e., yields of up to 90% of good purity. Thus, the process enables one to produce the tertiary-alkyl substituted cyclopentadienes with substantial efficiency.

The process may be exemplified by the following equation:

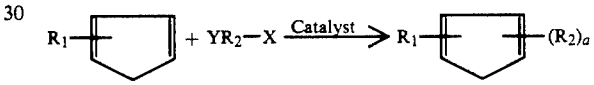

wherein in the above equation, $R_1$, $R_2$, and a are as described above, and Y is the number of moles of $R_2X$ used in the reaction, and X is a cleaving group, preferably halogen, preferably Br.

In the present invention it has been discovered that cyclopentadienes can be readily alkylated by tertiary-alkyl halides under phase transfer catalysis conditions using quaternary ammonium halides.

Steric effects on the reactivity of organmetallic complexes as a function of phosphine ligand structure have received substantial attention in the prior art but much less work on the steric effects of changing cyclopentadiene ligand structure has been reported, primarily because sterical bulky cyclopentadienes have not been readily available.

In the present invention, a phase transfer alkylation procedure has been discovered which provides excellent yields of good purity of the desired substituted cyclopentadiene. The phase transfer procedure of the present invention comprises reacting cyclopentadiene or alkyl substituted cyclopentadiene with a stoichiometric excess of a tertiary-alkyl halide and a base such as an alkali metal alkoxide or hydroxide using a phase transfer catalyst such as a quaternary ammonium halide.

The starting cyclopentadiene may be unsubstituted or may carry an alkyl substituent including other tertiary-alkyl substituents.

The starting cyclopentadiene is reacted with at least a stoichiometric excess of a tertiary alkyl halide in the presence of a base and a phase transfer agent. The tertiary alkyl halide is utilized in stoichiometric excess of at least 25% beyond the stoichiometrically required amount, and preferably is used in a molar ratio excess of at least 3:1 and most preferably 3:1 to 8:1.

The base utilized in the reaction is most preferably an aqueous solution of about 25 to 60 wt % of an alkali metal hydroxide such as potassium hydroxide or sodium hydroxide. The phase transfer catalyst is most preferably a quaternary ammonium halide is of the formula $NR_4X$, wherein X is halogen. The quaternary ammonium halide is utilized in a catalytic amount ranging from 1 to 50 mole % based on the amount of cyclopentadiene being reacted.

In conducting the reaction, cyclopentadiene or substituted cyclopentadiene and the tertiary-alkyl halide alkylating agent are added to a reaction vessel containing the basic solution such as an alkali metal aqueous solution and also containing a phase transfer catalytic agent, such as the quaternary ammonium halide. As pointed out above, it is preferred that the tertiary alkyl halide be utilized in excess and on a molar basis, the excess should range from about three to eight moles of tertiary-alkyl halide per mole of cyclopentadiene starting material.

In conducting the reaction, the mixture of cyclopentadiene starting material, t-alkyl halide, catalyst and base are permitted to react with vigorous stirring for a period of about one-half hour to ten hours. On completion of the reaction and cessation of agitation, the mixture is cooled, diluted, washed and dried.

In conducting the reaction by this phase transfer method, the preferred temperature ranges from about 20° to 120° C. and the residence time or reaction time is from one half hour up to three days. The molar ratio of tertiary alkyl halide to cyclopentadiene should range from about 3:1 up to about 8:1. The molar ratio of alkali metal hydroxide to cyclopentadiene reactant may range from 10:1 up to 100:1.

Suitable phase transfer catalysts include phosphonium salts, quaternary ammonium halide, n-alkyl $C_{12}$–$C_{16}$) dimethylbenzylammonium chloride, sold commercially as HYAMINE 3500, triethylbenzylammonium chloride, sold commercially as TEBAC, or a mixture of methyltrialkyl $C_8$ to $C_{10}$) ammonium chlorides, sold commercially as Adogen ® 464, tetrabutyl ammonium chloride, polyethyleneglycols and polyethers.

The invention is exemplified with reference to the preparation of tertiary butyl substituted cyclopentadiene. However, it will be recognized that the process of the invention as applicable to the use of analogous reactants to provide any desired tertiary alkyl group on the cyclopentadiene nucleus.

The following examples are presented to illustrate the invention but it is not to be considered as limited thereto. In the following examples, parts are by weight unless otherwise indicated.

EXAMPLE 1

In this example, freshly distilled cyclopentadiene, a 50 wt % aqueous solution of potassium hydroxide, and tertiary-butyl bromide in the molar ratio of 1:40:5 were stirred together in a reactor. The quaternary ammonium halide, Adogen ® 464 is added in the amount of one gram per mole of the potassium hydroxide. These reactants were stirred together and heated to 60° for 75 minutes and then at 100° for an additional 45 minutes. During the reaction foaming may occur which should be controlled. The reaction mixture is then cooled, diluted with pentane, washed with water and dried over magnesium sulfate. The pentane is then removed by vacuum. The crude residue contains the product and the Adogen ® 464. Chromatography of the crude material over silica gel yielded di(tert-butyl)-cyclopentadiene. The overall calculated yield is 90 wt % based on the starting cyclopentadiene material.

EXAMPLE 2

In this example, tri(tertiary-butyl)-cyclopentadiene is prepared directly by the reaction of cyclopentadiene and tertiary-butyl bromide by using a greater excess of tertiary butyl bromide in the reaction over that used in Example 1 and running the reaction longer and at higher temperatures. Otherwise, the reaction is carried out in the same manner as Example 1 to produce a mixture containing tri(tertiary-butyl)cyclopentadiene.

EXAMPLE 3

In this example, di(t-butyl)cyclopentadiene is alkylated to produce tri(t-butyl)cyclopentadiene. The procedure is essentially the same as in Example 1 except that the starting material is di(t-butyl) except that the starting material is di(t-butyl) cyclopentadiene and 55 wt % aqueous potassium hydroxide is used. The reaction is monitored by gas chromatography and additional t-butylbromide and Adogen ® 464 are added as needed until about half the mixture has been converted. After work-up to remove potassium hydroxide and the Adogen ® 464, and the decomposition products of Adogen ® 464, the di- and tri(t-butyl) cyclopentadienes are separated by distillation, yielding 50% of the tri(tertiary-butyl) cyclopentadiene, bp at 30 Torr, 135° to 140° C., and 30% of the di-tertiary-butyl cyclopentadiene starting material, bp at 30 Torr, 100° to 105° C.

Structure proofs relied primarily on $C_{13}$ and NMR analyses although elemental analysis was consistent with the empirical formula $C_{13}H_{22}$ di (t-butyl)cyclopentadiene and $C_{17}H_{30}$ for tri(t-butyl)cyclopentadiene. Chemical shifts and assignments are recorded in Table 1. In Table 1, it will be noted that di(t-butyl)cyclopentadiene exists as a mixture, the two major isomers being 1a and 1b in a 3:1 ratio as determined by gas chromatography. The identity of the two isomers is easily assigned from the $C_{13}$ NMR spectra of mixtures by the relative intensities of the resonances and the symmetry of 1b.

Tri(t-butyl)cyclopentadiene exists as a single isomer, 1,3,5-tri(1,1-dimethylethyl)cyclopentadiene. The downfield position of the ring C-5, 62.9 ppm compared with that found in 1a and 1b, 39.2 ppm, and 38.3 ppm, respectively, clearly signals that one of the t-butyl groups is on C-5. The reported position of the C-5 carbon in tetra(t-butyl)cyclopentadiene, 64.1 ppm in which one t-butyl is also presumed to be on the C-5 supports the assignment.

The predominance of the 1,3,5-isomer arises since it is the only arrangement which does not place t-butyls on three adjacent carbons nor two t-butyls on adjacent $sp^2$ carbons. For less sterically bulky substituents, n-alkyl groups, trialkyl derivatives are also single isomers, but are the 1,2,4- rather than the 1,3,5- isomers thus placing all three alkyl groups on $sp^2$ carbons.

The conditions under which these reactions are run, using a strong base in the presence of a phase transfer catalyst inevitably favor elimination reactions with tertiary substrates. Consequently, the operation of previously recognized substitution mechanisms involving tertiary halide seems unlikely. The fact that alkylation competes so favorably with elimination argues for a unique reaction pathway involving cyclopentadiene prior to the rate determining step. The prior art teaches that tertiary alkyl halides are not appropriate reagents in phase transfer catalyzed reactions.

Table 1 is as follows:

TABLE 1

| | 13C NMR ASSIGNMENTS[a] | | |
|---|---|---|---|
| | COMPOUND | | |
| POSITION | 1a[b] | 1b[b] | 2 |
| C-1 | 159.1 | 155.8 | 159.6 |
| C-2 | 123.7 | 123.2 | 129.2 |
| C-3 | 156.1 | 123.2 | 153.5 |
| C-4 | 119.4 | 155.8 | 126.2 |
| C-5 | 39.1 | 38.2 | 62.9 |
| $\underline{C}(CH_3)_3$; ring position in parenthesis | 33.1 (1) 32.1 (3) | 33.1 (1) | 34.0 (5) 33.8 (1) 31.8 (3) |
| $C(\underline{C}H_3)_3$; ring position in parenthesis | 29.7 (1) | 30.9 (1) 30.9 (3) | 32.0 (1) 30.3 (3) 29.6 (5) |

[a]Assignments made by 13C-SAT (Varian), 1H - 13C N difference, and DEPT techniques.
[b]Analysis performed on a mixture of 1a and 1b. The relative intensities of peaks in each region of the spectrum were used to assign resonances to either 1a or 1b.

The invention has been described herein with reference to certain preferred embodiments. However, it is obvious variations thereon will become apparent to those skilled in the art, the invention is not to be considered as limited thereto.

What is claimed is:

1. Tertiary alkyl substituted cyclopentadienes of the following formula:

wherein $R_1$ is hydrogen or non-tertiary alkyl of 1 to 4 carbon atoms, $R_2$ is tertiary-alkyl of 4 to 12 carbon atoms, and a is 2 or 3, with the proviso that when $R_1$ is hydrogen, a is 3 and $R_2$ is attached to the cyclopentadiene ring through a tertiary carbon.

2. A compound according to claim 1 wherein $R_1$ is hydrogen and $R_2$ is tertiary-butyl.

3. Tertiary substituted cyclopentadiene of the following formula:

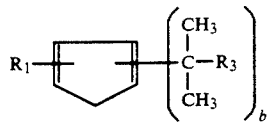

wherein $R_1$ is hydrogen or alkyl of 1 to 4 carbon atoms, $R_3$ is straight or branch chained alkyl of 2 to 9 carbon atoms, and b is 1 to 4, provided that when $R_1$ is H, b is at least 2.

4. Cyclopentadienes of claim 3 wherein b is 1 to 3.

5. The cyclopentadiene of claim 3 wherein $R_1$ is 14 and b is 2 or 3.

6. A method for the preparation of an alkylated cyclopentadiene wherein the cyclopentadiene ring is alkylated by at least two tertiary-alkyl groups attached to the cyclopentadiene ring through a tertiary carbon, which comprises the reaction of cyclopentadiene with a stoichiometric excess of a saturated tertiary-alkyl halide, in the presence of a strong base catalyst and a phase transfer agent at an elevated temperature with vigorous agitation, and wherein the amount of said phase transfer agent is about 1 to 50 mole % of the amount of cyclopentadiene being reacted.

7. A method according to claim 6, wherein the reaction is carried out at an elevated temperature over a period of thirty minutes to three days and the phase transfer agent is a quaternary ammonium halide.

8. A method according to claim 6 wherein a molar excess of tertiary-alkyl halide of at least 3:1 is used in the reaction.

9. A method according to claim 6 wherein the tertiaryalkyl halide is t-butyl bromide.

10. A synthetic lubricating composition comprising a tertiary alkyl substituted cyclopentadiene of the following formula:

wherein $R_1$ is hydrogen or an alkyl of 1 to 4 carbon atoms, $R_2$ is tertiary-alkyl of 4 to 10 carbon atoms, and a is 1 or 5, and is attached to the cyclopentadiene ring through a tertiary carbon, in combination with a lubricating additive, providing that the number of carbons in $R_1$ plus a times the number of carbons in $R_2 \geq 12$.

11. A synthetic lubricating composition according to claim 10 which also contains from 0.01 to 40% by weight of a lubricating oil additive.

* * * * *

UNITED STATES PATENT AND TRADEMARK OFFICE
CERTIFICATE OF CORRECTION

PATENT NO. : 5,144,095
DATED : September 1, 1992
INVENTOR(S) : VENIER et al

It is certified that error appears in the above-identified patent and that said Letters Patent is hereby corrected as shown below:

Column 8:
    Claim 5, line 1, change "14" to --hydrogen--.
    Claim 10, line 13, change "1 or 5" to --1 to 5--.

Signed and Sealed this

Ninth Day of November, 1993

Attest:

BRUCE LEHMAN

Attesting Officer      Commissioner of Patents and Trademarks